United States Patent
Kamon et al.

(10) Patent No.: US 11,992,178 B2
(45) Date of Patent: May 28, 2024

(54) IMAGE PROCESSING DEVICE, ENDOSCOPE SYSTEM, AND IMAGE PROCESSING METHOD

(71) Applicant: FUJIFILM Corporation, Tokyo (JP)

(72) Inventors: Shumpei Kamon, Kanagawa (JP); Hirona Yumbe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 858 days.

(21) Appl. No.: 17/035,738

(22) Filed: Sep. 29, 2020

(65) Prior Publication Data
US 2021/0012495 A1 Jan. 14, 2021

Related U.S. Application Data

(63) Continuation of application No. PCT/JP2019/015134, filed on Apr. 5, 2019.

(30) Foreign Application Priority Data

Apr. 13, 2018 (JP) ................................. 2018-077661

(51) Int. Cl.
*A61B 1/00* (2006.01)
*G06T 7/00* (2017.01)

(52) U.S. Cl.
CPC .... *A61B 1/000096* (2022.02); *A61B 1/00018* (2013.01); *A61B 1/0002* (2013.01);
(Continued)

(58) Field of Classification Search
CPC .......... A61B 1/000096; A61B 1/00018; A61B 1/0002; A61B 1/045; G06T 7/0012;
(Continued)

(56) References Cited

U.S. PATENT DOCUMENTS

| 9,411,932 B2 | 8/2016 | Nishiyama |
| 9,684,849 B2 | 6/2017 | Yaguchi |

(Continued)

FOREIGN PATENT DOCUMENTS

| CN | 101912251 | 12/2010 |
| EP | 1922977 | 5/2008 |

(Continued)

OTHER PUBLICATIONS

"Office Action of Japan Counterpart Application" with English translation thereof, dated May 13, 2022, p. 1-p. 16.
(Continued)

*Primary Examiner* — Dhaval V Patel
(74) *Attorney, Agent, or Firm* — JCIPRNET

(57) ABSTRACT

An object of the present invention is to provide an image processing device, an endoscope system, and an image processing method capable of efficiently saving a moving image in which a lesion is shown. An image processing device according to a first aspect of the present invention includes a moving image acquisition unit that acquires an examination moving image by an endoscope, a report information acquisition unit that acquires report information on an examination corresponding to the examination moving image, the report information including at least one of subject information of a still image acquired in the examination or acquisition time information of the still image, a report information analysis unit that extracts at least one of subject information of a lesion image or acquisition time information of the lesion image from the report information, and a moving image saving unit that saves a lesion moving image, which is a moving image for a time range in which the lesion image is included in the examination moving image, on the basis of a result of the extraction.

9 Claims, 14 Drawing Sheets

(52) U.S. Cl.
CPC .. *G06T 7/0012* (2013.01); *G06T 2207/10068* (2013.01); *G06T 2207/30096* (2013.01)

(58) Field of Classification Search
CPC .......... G06T 2207/10068; G06T 2207/30096; G02B 23/24; G16H 30/40; G16H 40/60; G16H 50/20

See application file for complete search history.

(56) References Cited

U.S. PATENT DOCUMENTS

| | | | |
|---|---|---|---|
| 10,825,178 B1* | 11/2020 | Jeong | G06N 20/00 |
| 11,523,741 B2* | 12/2022 | Okiyama | A61B 5/0062 |
| 2008/0242926 A1 | 10/2008 | Nishino | |
| 2008/0303898 A1 | 12/2008 | Nishimura | |
| 2009/0019381 A1 | 1/2009 | Kimoto | |
| 2009/0051691 A1 | 2/2009 | Kimoto | |
| 2013/0155216 A1 | 6/2013 | Kasumi | |
| 2014/0063215 A1 | 3/2014 | Miura | |
| 2015/0272429 A1 | 10/2015 | Shigeta | |
| 2016/0048637 A1 | 2/2016 | Nishiyama | |
| 2020/0193595 A1* | 6/2020 | Iwamura | G16H 10/60 |
| 2020/0279368 A1* | 9/2020 | Tada | G06T 7/0012 |
| 2021/0345865 A1* | 11/2021 | Spillinger | G06T 7/0012 |

FOREIGN PATENT DOCUMENTS

| | | |
|---|---|---|
| EP | 1922984 | 5/2008 |
| EP | 2926717 | 10/2015 |
| JP | 2007075163 | 3/2007 |
| JP | 2008237640 | 10/2008 |
| JP | 2008301968 | 12/2008 |
| JP | 2012014129 | 1/2012 |
| JP | 2014042727 | 3/2014 |
| JP | 2014079562 | 5/2014 |
| JP | 2014147483 | 8/2014 |
| JP | 2015195845 | 11/2015 |
| WO | 2012165381 | 12/2012 |
| WO | 2015020093 | 2/2015 |
| WO | 2015029584 | 3/2015 |
| WO | 2017104192 | 6/2017 |

OTHER PUBLICATIONS

"Search Report of Europe Counterpart Application", dated Aug. 23, 2021, p. 1-p. 29.

Office Action of Japan Counterpart Application, with English translation thereof, dated Feb. 4, 2022, pp. 1-17.

Office Action of Japan Counterpart Application, with English translation thereof, dated Nov. 9, 2021, pp. 1-12.

"International Search Report (Form PCT/ISA/210) of PCT/JP2019/015134," dated Jul. 2, 2019, with English translation thereof, pp. 1-4.

"Written Opinion of the International Searching Authority (Form PCT/ISA/237) of PCT/JP2019/015134," dated Jul. 2, 2019, with English translation thereof, pp. 1-10.

Office Action of European Counterpart Application, dated Jul. 11, 2023, pp. 1-7.

"Office Action of China Counterpart Application", dated Jul. 23, 2023, with English translation thereof, p. 1-p. 20.

* cited by examiner

IMAGE PROCESSING DEVICE, ENDOSCOPE SYSTEM, AND IMAGE PROCESSING METHOD

CROSS-REFERENCE TO RELATED APPLICATIONS

The present application is a Continuation of PCT International Application No. PCT/JP2019/015134 filed on Apr. 5, 2019 claiming priority under 35 U.S.C § 119(a) to Japanese Patent Application No. 2018-077661 filed on Apr. 13, 2018. Each of the above applications is hereby expressly incorporated by reference, in its entirety, into the present application.

BACKGROUND OF THE INVENTION

1. Field of the Invention

The present invention relates to an image processing device, an endoscope system, and an image processing method, and particularly to an image processing device, an endoscope system, and an image processing method for processing a moving image acquired by an endoscopic examination.

2. Description of the Related Art

In a case where an examination is performed using an endoscope, many moving images and still images are captured. The captured images are used for various purposes such as diagnosis support and report creation, and different images are required depending on the purpose of use, so that various images are captured over a long period of time during the examination process. However, in a case where all such images are saved as they are, the storage capacity becomes too large. Therefore, a technique for reducing the amount of image data has been proposed.

For example, JP2014-042727A discloses that moving image data is compressed at a compression rate according to the degree of importance to reduce the amount of data while maintaining the image quality of the important moving image data. JP2008-237640A discloses a capsule endoscope in which the number of times of imaging is reduced in a portion apart from a lesion (region of interest) and the number of times of imaging is increased in the vicinity of the region of interest. WO2015/029584A discloses that a moving image for a time range before and after a frame in which still images are captured is saved.

SUMMARY OF THE INVENTION

Although the above-mentioned JP2014-042727A discloses that the compression rate is set according to examination type information, the "examination type information" is information on an examination type (screening, procedure, and the like) that is known in advance. Further, "diagnosis information" disclosed in JP2008-237640A is position information of a polyp that has been found in a past examination. Using information on such past examinations and diagnoses, it is not possible to consider information on lesions (regions of interest) found by new examinations, and images of such lesions may not be properly saved. In JP2008-237640A, it is necessary to detect a region of interest from images acquired during an examination in order to save (record) a frame in which a lesion is shown and frames before and after the frame, and in a case where the detection fails, it is difficult to save the image. Further, since still images acquired by an endoscopic examination also include many images in which a lesion is not shown, in a case where frames before and after acquisition of the still image are saved as in WO2015/029584A, the amount of data may be increased by recording a large amount of moving images in which a lesion is not shown.

As described above, it is difficult for the technique in the related art to efficiently save a moving image in which a lesion is shown.

The present invention has been made in view of such circumstances, and an object thereof is to provide an image processing device, an endoscope system, and an image processing method capable of efficiently saving a moving image in which a lesion is shown.

In order to achieve the above-described object, there is provided an image processing device according to a first aspect of the present invention comprising: a moving image acquisition unit that acquires an examination moving image by an endoscope; a report information acquisition unit that acquires report information on an examination corresponding to the examination moving image, the report information including at least one of subject information of a still image acquired in the examination or acquisition time information of the still image; a report information analysis unit that extracts at least one of subject information of a lesion image or acquisition time information of the lesion image from the report information; and a moving image saving unit that saves a lesion moving image, which is a moving image for a time range in which the lesion image is included in the examination moving image, on the basis of a result of the extraction.

In the first aspect, since report information including at least one of image information of a still image acquired in the examination or acquisition time information is acquired, and at least one of image information or acquisition time information of a lesion image (image in which a lesion is shown) from the report information is acquired, it is possible to acquire information on the lesion image even in a case where the lesion is not shown in the still image included in the report information. In the first aspect, since the lesion moving image which is the moving image for the time range in which the lesion image is included in the examination moving image is saved, it is possible to prevent the amount of data from increasing by saving the moving image for a long time in the time range in which a region of interest is not shown. Further, in the first aspect, since the report information "on the examination corresponding to the examination moving image" is acquired, it is possible to consider information on a new lesion found in the examination. The lesion moving image can be saved by a method such as once saving images in a temporary storage area and saving necessary portions in a normal storage area or saving the images in a storage area and erasing unnecessary portions.

As described above, according to the first aspect, it is possible to efficiently save a moving image in which a lesion is shown (lesion moving image). In the first aspect and each of the following aspects, "subject information" is information (position, size, type, and the like of the subject) on a subject (lesion in the case of a lesion image) shown in the image, and "acquisition time information" is information that can specify the timing of image acquisition in an examination, such as an absolute time when an image is captured (Japan Standard Time, or the like), an elapsed time from the start of capturing a moving image of a frame where an image is captured, or a count number of a counter indicating an imaging time.

In the lesion moving image to be saved, the time width before and after the lesion image can be set in consideration of the amount of data of the moving image and the like.

In the first aspect and each of the following aspects, the examination moving image, the still image, the lesion image, and the lesion moving image are one aspect of an image for medical use (also referred to as a medical image). In a case of capturing such an image for medical use, a light source that generates light in a white range, light including a plurality of wavelengths (narrow-band light) as a white range, infrared light, or excitation light can be used. In addition, an image for medical use to be acquired may be a normal light image obtained by irradiation with light in a white range or light in a plurality of wavelength ranges as light in a white range, or may be a special light image having information on a specific wavelength range acquired on the basis of the normal light image.

In a second aspect of the image processing device according to the first aspect, the report information acquisition unit acquires the report information including lesion information indicating whether the still image is the lesion image, and the report information analysis unit extracts the subject information and/or the acquisition time information of the lesion image on the basis of the lesion information. The second aspect defines the specific aspect of the content of the report information and the analysis method.

In a third aspect of the image processing device according to the first or second aspect, the moving image saving unit determines whether to save the lesion moving image on the basis of the result of the extraction. In the third aspect, the moving image saving unit can determine whether to save the lesion moving image on the basis of the length of time that the lesion image is included, the proportion of the entire examination moving image, and the like. For example, it is possible to perform processing for "saving the lesion moving image in a case where the examination moving image includes the lesion image, and not saving the lesion moving image in a case where it does not include (or hardly includes) the lesion image".

In a fourth aspect of the image processing device according to any one of the first to third aspects, the report information analysis unit matches the subject information included in the report information with the examination moving image to determine the time range in which the lesion image is included in the examination moving image, and the moving image saving unit saves the lesion moving image for the determined time range. As in the fourth aspect, by matching the images, the time range in which the lesion is shown can be cut out as a motion picture.

In a fifth aspect of the image processing device according to any one of the first to fourth aspects, the report information analysis unit extracts the acquisition time information of the lesion image, and the moving image saving unit saves the examination moving image on the basis of the extracted acquisition time information. The fifth aspect defines an aspect in which a motion picture is cut out based on the acquisition time information (synonymous with that in the first aspect).

In a sixth aspect of the image processing device according to any one of the first to fifth aspects, the report information acquisition unit acquires acquisition time information input by a user as the acquisition time information of the still image, and the report information analysis unit extracts the acquisition time information acquired by the report information acquisition unit as the acquisition time information of the lesion image. In the present invention, the moving image may be saved on the basis of the information input by the user as in the sixth aspect. For example, such processing can be performed in a case where the information on the lesion image cannot be properly extracted.

In a seventh aspect of the image processing device according to any one of the first to sixth aspects, the moving image saving unit saves each of time ranges in which different lesions are shown in the examination moving image as an independent moving image. According to the seventh aspect, it is possible to easily manage a moving image according to a lesion, use a moving image including a desired lesion, and the like.

In an eighth aspect of the image processing device according to any one of the first to seventh aspects, in a case of saving the lesion moving image for the examination moving image, the moving image saving unit saves a small-capacity moving image having a smaller data capacity than the examination moving image by subjecting the examination moving image to processing for reducing a frame rate outside the time range and/or processing for reducing a resolution outside the time range. By changing the frame rate and the resolution to reduce the data capacity as in the eighth aspect, it is possible to more efficiently save the moving image in which the lesion is shown.

In order to achieve the above-described object, there is provided an endoscope system according to a ninth aspect of the present invention comprising: the image processing device according to any one of the first to eighth aspects, an endoscope including an insertion part to be inserted into a subject and a hand operation part connected to a proximal end of the insertion part, the insertion part including a distal end rigid portion, a bendable portion connected to a proximal end of the distal end rigid portion, and a flexible portion connected to a proximal end of the bendable portion; and an imaging unit including an imaging lens that is provided in the distal end rigid portion to form an optical image of the subject, and an imaging element on which the optical image is formed by the imaging lens. The moving image acquisition unit acquires the examination moving image captured by the imaging unit. In the endoscope system according to the ninth aspect, by comprising the image processing device according to any one of the first to eighth aspects, it is possible to efficiently save a moving image in which a region of interest is shown (lesion moving image).

In order to achieve the above-described object, there is provided an image processing method according to a tenth aspect of the present invention comprising: a moving image acquisition step of acquiring an examination moving image by an endoscope; a report information acquisition step of acquiring report information on an examination corresponding to the examination moving image, the report information including at least one of subject information of a still image acquired in the examination or acquisition time information of the still image; a report information analysis step of extracting at least one of subject information of a lesion image or acquisition time information of the lesion image from the report information; and a moving image saving step of saving a lesion moving image, which is a moving image for a time range in which the lesion image is included in the examination moving image, on the basis of a result of the extraction. According to the tenth aspect, it is possible to efficiently save a moving image in which a region of interest is shown (lesion moving image) as in the first aspect.

The configuration of the tenth aspect may further include a configuration similar to that of the second to eighth aspects. In addition, a program for causing the endoscope system to execute the image processing method of these aspects and a non-transitory recording medium in which a computer-readable code of the program is recorded can also be mentioned as aspects of the present invention.

As described above, with the image processing device, the endoscope system, and the image processing method according to the aspects of the present invention, it is possible to efficiently save a moving image in which a region of interest is shown.

BRIEF DESCRIPTION OF THE DRAWINGS

FIG. 16 is a diagram showing still another example of identifying and displaying the lesion.

DESCRIPTION OF THE PREFERRED EMBODIMENTS

Hereinafter, an embodiment of an image processing device, an endoscope system, and an image processing method according to the embodiment of the present invention will be described in detail with reference to the accompanying drawings.

First Embodiment

Figure 1:
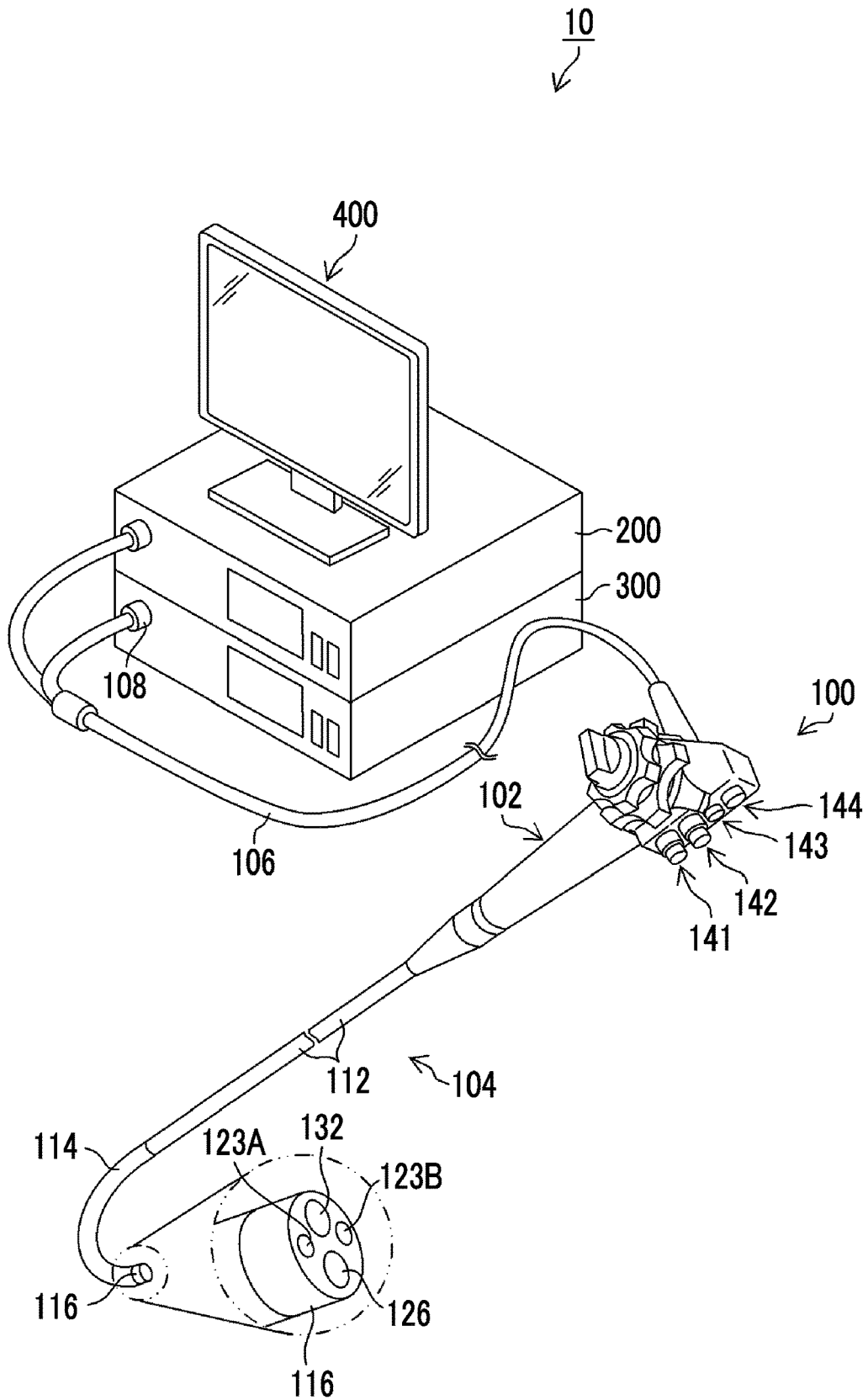
FIG. 1 is an external view illustrating an endoscope system according to a first embodiment.
Figure 2:
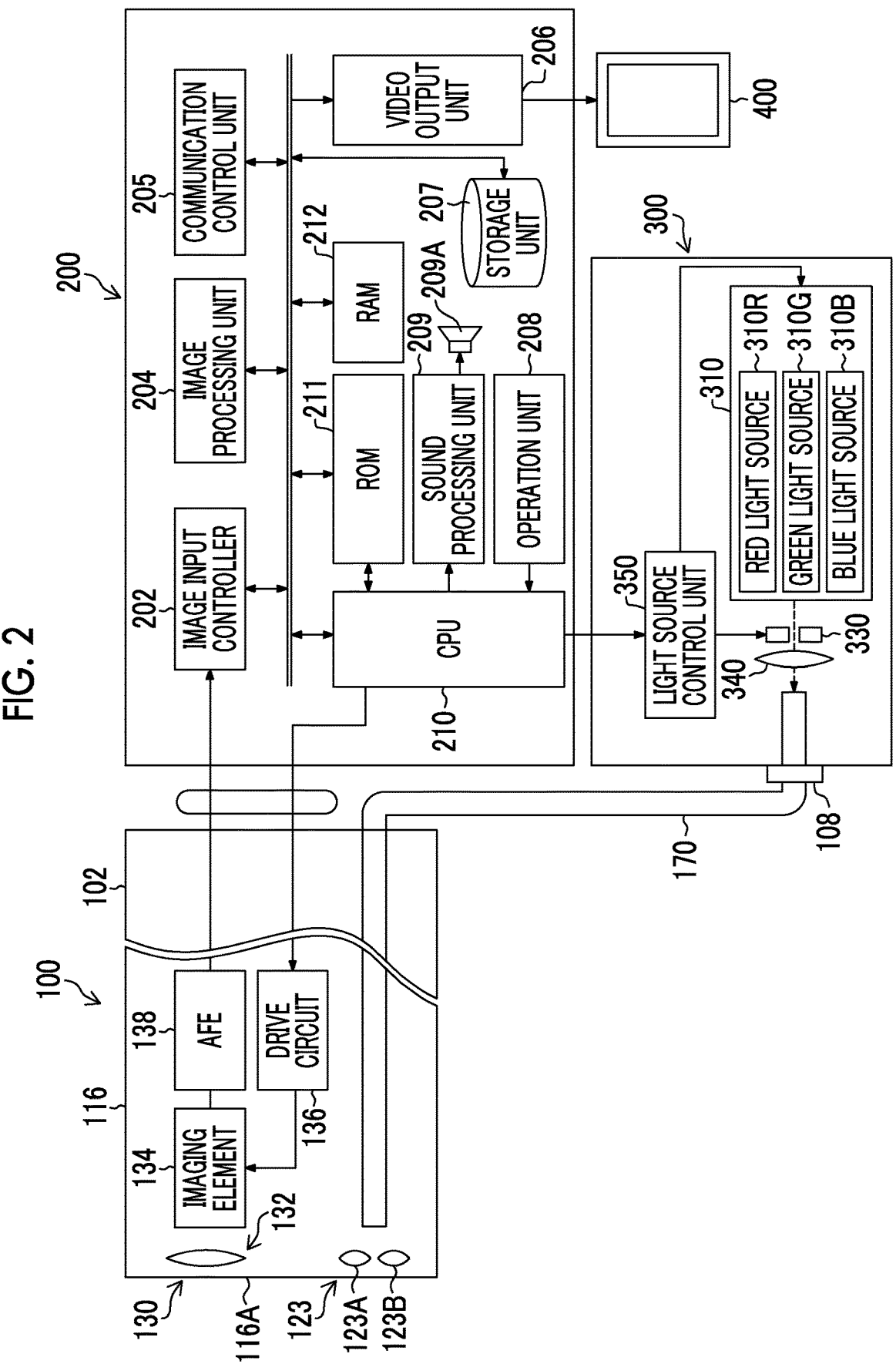
FIG. 2 is a block diagram showing a configuration of the endoscope system.

FIG. 1 is an external view showing an endoscope system 10 (image processing device, diagnosis support device, endoscope system, medical image processing device) according to a first embodiment, and FIG. 2 is a block diagram showing a configuration of the main part of the endoscope system 10. As shown in FIGS. 1 and 2, the endoscope system 10 is configured to include an endoscope main body 100 (endoscope), a processor 200 (processor, image processing device, medical image processing device), a light source device 300 (light source device), and a monitor 400 (display device).

<Configuration of Endoscope Main Body>

The endoscope main body 100 comprises a hand operation part 102 (hand operation part) and an insertion part 104 (insertion part) connected to the hand operation part 102. An operator (user) grasps and operates the hand operation part 102, and inserts the insertion part 104 into the body of a subject (living body) to observe the subject. In addition, the hand operation part 102 is provided with an air supply and water supply button 141, a suction button 142, a function button 143 to which various functions are assigned, and an imaging button 144 that receives an imaging instruction operation. The insertion part 104 is configured to include a flexible portion 112 (flexible portion), a bendable portion 114 (a bendable portion), and a distal end rigid portion 116 (distal end rigid portion) in this order from the hand operation part 102 side. That is, the bendable portion 114 is connected to a proximal end of the distal end rigid portion 116, and the flexible portion 112 is connected to a proximal end of the bendable portion 114. The hand operation part 102 is connected to the proximal end of the insertion part 104. The user can bend the bendable portion 114 by operating the hand operation part 102 to change the direction of the distal end rigid portion 116 vertically and horizontally. The distal end rigid portion 116 is provided with an imaging optical system 130 (imaging unit), an illumination part 123, a forceps port 126, and the like (refer to FIGS. 1 to 3).

During observation and treatment, white light and/or narrow-band light (one or more of red narrow-band light, green narrow-band light, and blue narrow-band light) can be irradiated from illuminating lenses 123A and 123B of the illumination part 123 by operating an operation unit 208 (refer to FIG. 2). In addition, by the operation of the air supply and water supply button 141, cleaning water is discharged from a water supply nozzle (not shown), and an imaging lens 132 (imaging lens) and the illuminating lenses 123A and 123B of the imaging optical system 130 can be cleaned. A pipe line (not shown) is communicated with the forceps port 126 opened at the distal end rigid portion 116, and a treatment tool (not shown) for tumor excision or the like is inserted into the pipe line and is appropriately moved forward and backward to perform a necessary treatment on the subject.

Figure 3:
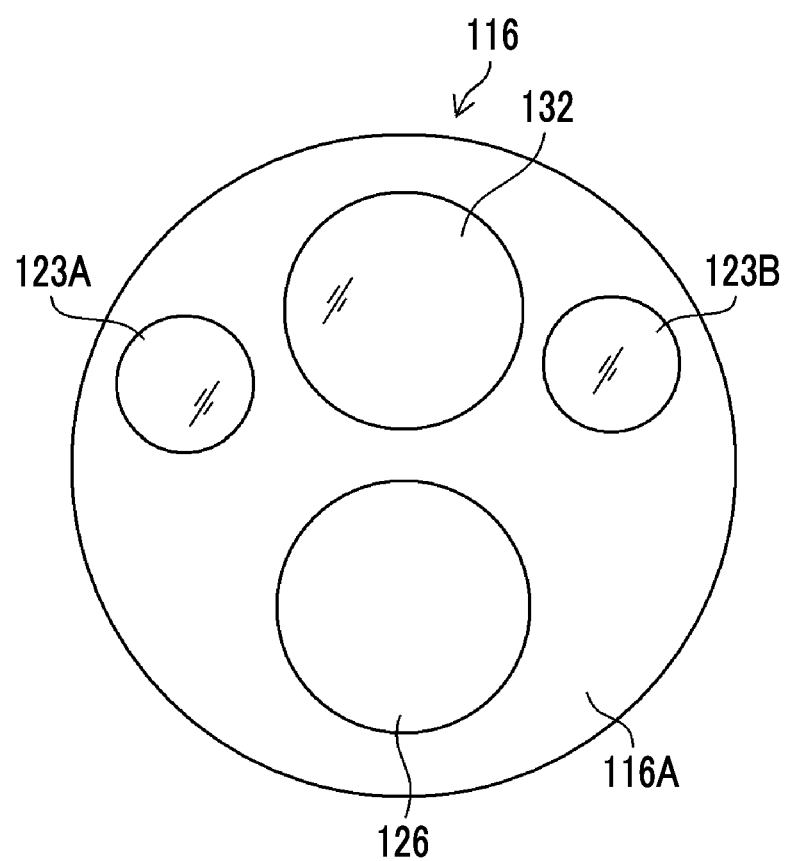
FIG. 3 is a diagram showing a configuration of a distal end rigid portion of an endoscope.

As shown in FIGS. 1 to 3, the imaging lens 132 (imaging unit) is arranged on a distal end side end surface 116A of the distal end rigid portion 116. A complementary metal-oxide semiconductor (CMOS) type imaging element 134 (imaging element, imaging unit), a drive circuit 136, and an analog front end (AFE) 138 are arranged at the back of the imaging lens 132, and an image signal is output by these elements. The imaging element 134 is a color image pickup element and comprises a plurality of pixels composed of a plurality of light-receiving elements disposed in a matrix (two-dimensionally arrayed) in a specific pattern array (Bayer array, X-Trans (registered trademark) array, honeycomb array, or the like). Each pixel of the imaging element 134 includes a microlens, a red (R), green (G), or blue (B) color filter, and a photoelectric conversion part (photodiode or the like). The imaging optical system 130 can generate a color image from pixel signals of three colors of red, green, and blue, or can generate an image from pixel signals of any one or two colors of red, green, and blue. In the first embodiment, a case where the imaging element 134 is a CMOS type imaging element will be described, but the imaging element 134 may be a charge coupled device (CCD) type imaging element. Each pixel of the imaging element 134 may further comprise a violet color filter corresponding to a violet light source and/or an infrared filter corresponding to an infrared light source.

An optical image of a subject (tumor part, lesion part) is formed on a light-receiving surface (imaging surface) of the imaging element 134 by the imaging lens 132, converted into an electric signal, output to the processor 200 via a signal cable (not shown), and converted into a video signal. As a result, an observation image is displayed on the monitor 400 connected to the processor 200.

In addition, the illuminating lenses 123A (for visible light) and 123B (for infrared light) of the illumination part 123 are provided adjacent to the imaging lens 132 on the distal end side end surface 116A of the distal end rigid portion 116. At the back of the illuminating lenses 123A and 123B, an emission end of a light guide 170 described later is arranged, the light guide 170 is inserted into the insertion part 104, the hand operation part 102, and a universal cable 106, and an incident end of the light guide 170 is disposed in a light guide connector 108.

<Configuration of Light Source Device>

As shown in FIG. 2, the light source device 300 is configured to include a light source 310 for illumination, a stop 330, a condensing lens 340, a light source control unit 350, and the like, and allows observation light to enter the light guide 170. The light source 310 comprises a red light source 310R, a green light source 310G, and a blue light source 310B that respectively perform irradiation with red, green, and blue narrow-band lights, and can perform irradiation with red, green, and blue narrow-band lights. The illuminance of the observation light by the light source 310 is controlled by the light source control unit 350, and the illuminance of the observation light can be lowered and the illumination can be stopped as necessary.

The light source 310 can emit red, green, and blue narrow-band lights in any combination. For example, white light (normal light) can be irradiated as observation light by simultaneously emitting red, green, and blue narrow-band lights, or narrow-band light (special light) can be irradiated by emitting one or two of them. The light source 310 may further comprise the violet light source that performs irradiation with violet light (an example of narrow-band light) and the infrared light source that performs irradiation with infrared light (an example of narrow-band light). In addition, white light or narrow-band light may be irradiated as observation light by a light source that performs irradiation with white light and a filter that transmits the white light and each narrow-band light.

<Wavelength Range of Light Source>

The light source 310 may be a light source that generates light in a white range or light in a plurality of wavelength ranges as light in a white range, and alternatively may be a light source that generates light in a specific wavelength range narrower than a white wavelength range. The specific wavelength range may be a blue range or a green range in a visible range, or a red range in a visible range. In a case where the specific wavelength range is the blue range or the green range in the visible range, the specific wavelength range includes a wavelength range of 390 nm to 450 nm, or 530 nm to 550 nm, and may have a peak wavelength in a wavelength range of 390 nm to 450 nm, or 530 nm to 550 nm. In addition, in a case where the specific wavelength range is the red range in the visible range, the specific wavelength range includes a wavelength range of 585 nm to 615 nm, or 610 nm to 730 nm, and light in the specific wavelength range may have a peak wavelength in a wavelength range of 585 nm to 615 nm, or 610 nm to 730 nm.

The light of the specific wavelength range described above includes a wavelength range in which light absorption coefficients of oxygenated hemoglobin and reduced hemoglobin are different, and may have a peak wavelength in the wavelength range in which the light absorption coefficients of oxygenated hemoglobin and reduced hemoglobin are different. In this case, the specific wavelength range includes a wavelength range of 400±10 nm, 440±10 nm, 470±10 nm, or 600 nm to 750 nm, and may have a peak wavelength in a wavelength range of 400±10 nm, 440±10 nm, 470±10 nm, or 600 nm to 750 nm.

In addition, the light generated by the light source 310 includes a wavelength range of 790 nm to 820 nm or 905 nm to 970 nm, and may have a peak wavelength in a wavelength range of 790 nm to 820 nm or 905 nm to 970 nm.

The light source 310 may comprise a light source that performs irradiation with excitation light having a peak of 390 nm to 470 nm. In this case, an image for medical use (in-vivo image) having information on fluorescence emitted by a fluorescent material in the subject (living body) can be acquired. In a case of acquiring a fluorescence image, a coloring agent for a fluorescence method (such as fluorescein and acridine orange) may be used.

A light source type (a laser light source, a xenon light source, a light-emitting diode (LED) light source, and the like), a wavelength, presence or absence of a filter, and the like of the light source 310 are preferably configured according to a type of the subject, a purpose of observation, and the like. In addition, at the time of observation, the wavelength of the observation light is preferably combined and/or switched according to a type of the subject, a purpose of observation, and the like. In a case where the wavelength is switched, the wavelength of the light to be irradiated may be switched by, for example, rotating a disk-shaped filter (a rotary color filter) that is disposed in front of the light source and provided with a filter that transmits or blocks light having a specific wavelength.

In addition, the imaging element used in carrying out the present invention is not limited to a color image pickup element in which a color filter is arranged for each pixel as in the imaging element 134, and may be a monochrome imaging element. In a case of using the monochrome imaging element, it is possible to capture an image in a field-sequential (color-sequential) manner by sequentially switching the wavelength of observation light. For example, the wavelength of the emitted observation light may be sequentially switched among (blue, green, and red), or the wavelength of the observation light emitted by the rotary color filter (red, green, blue, or the like) may be switched by irradiation with broadband light (white light). In addition, the wavelength of the observation light emitted by the rotary color filter (green, blue, or the like) may be switched by irradiation with one or a plurality of narrow-band lights (green, blue, or the like). The narrow-band light may be infrared light (first narrow-band light, second narrow-band light) having two or more different wavelengths.

By connecting the light guide connector 108 (refer to FIG. 1) to the light source device 300, observation light irradiated from the light source device 300 is transmitted to the illuminating lenses 123A and 123B via the light guide 170, and is irradiated from the illuminating lenses 123A and 123B to the observation range.

<Configuration of Processor>

A configuration of the processor 200 will be described with reference to FIG. 2. The processor 200 inputs an image signal (image signal of a moving image and/or a still image) output from the endoscope main body 100 via an image input controller 202, performs necessary image processing in an image processing unit 204, and outputs the image signal via a video output unit 206. As a result, an observation image (in-vivo image) is displayed on the monitor 400 (display device). In addition, the processor 200 performs a report information and analysis, an analysis of a lesion moving image, and the like. These processes are performed under control of a central processing unit (CPU) 210. That is, the CPU 210 has functions as a moving image acquisition unit, a report information acquisition unit, a report information analysis unit, and a moving image saving unit. A storage unit 207 stores an image (moving image, still image) of a subject, acquired report information, its analysis result, and the like (described later). Under the control of the CPU 210 and the image processing unit 204, a sound processing unit 209 outputs a message (sound) or the like according to the result of detection and/or classification of a region of interest from a speaker 209A.

A read only memory (ROM) 211 is a nonvolatile storage element (non-transitory recording medium), and stores a computer-readable code of a program for causing the CPU 210 and/or the image processing unit 204 (image processing device, computer) to execute the image processing method according to the embodiment of the present invention. A random access memory (RAM) 212 is a storage element for temporary storage during various types of processing, and can also be used as a buffer during image acquisition.

<Function of Image Processing Unit>

Figure 4:
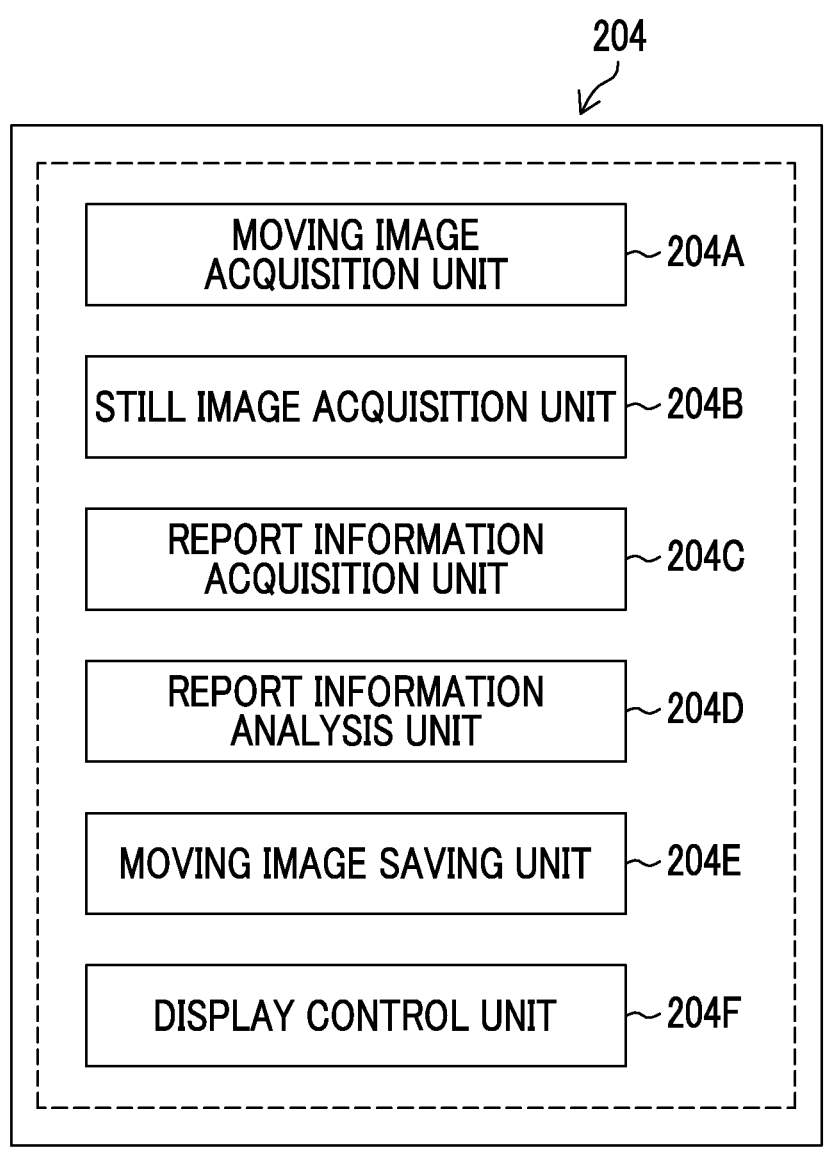
FIG. 4 is a diagram showing a functional configuration of an image processing unit.

FIG. 4 is a diagram showing a functional configuration of the image processing unit 204 (medical image acquisition unit, medical image analysis processing unit, medical image analysis result acquisition unit). The image processing unit 204 includes a moving image acquisition unit 204A (moving image acquisition unit), a still image acquisition unit 204B, a report information acquisition unit 204C (report information acquisition unit), a report information analysis unit 204D (report information analysis unit), a moving image saving unit 204E (moving image saving unit), and a display control unit 204F (image correction unit). The report information analysis unit 204D also operates as a medical image analysis processing unit.

The image processing unit 204 may comprise a special light image acquisition unit that acquires a special light image having information on a specific wavelength range on the basis of a normal light image obtained by irradiation with light in a white range or light in a plurality of wavelength ranges as light in a white range. In this case, the signal of the specific wavelength range can be obtained by calculation based on color information of RGB (R: red, G: green, B: blue) or CMY (C: cyan, M: magenta, Y: yellow) included in the normal light image.

The image processing unit 204 may comprise a feature quantity image generation unit that generates a feature quantity image by calculation based on at least one of a normal light image obtained by irradiation with light in a white range or light in a plurality of wavelength ranges as light in a white range or a special light image obtained by irradiation with light in a specific wavelength range, and may acquire and display the feature quantity image as an image for medical use (medical image).

Details of the processing by these functions of the image processing unit 204 will be described later. The processing by these functions is performed under the control of the CPU 210.

The function of the image processing unit 204 described above can be realized by using various processors. The various processors include, for example, a central processing unit (CPU) that is a general-purpose processor that executes software (program) to realize various functions. In addition, the above-described various processors include a programmable logic device (PLD) which is a processor whose circuit configuration can be changed after manufacturing, such as a graphics processing unit (GPU) and a field programmable gate array (FPGA) which are processors specialized for image processing. Further, the above-described various processors also include a dedicated electric circuit which is a processor having a dedicated circuit configuration for executing specific processing such as an application specific integrated circuit (ASIC).

The function of each unit may be realized by one processor, or may be realized by a plurality of processors of the same type or different types (for example, a plurality of FPGAs, a combination of a CPU and an FPGA, or a combination of a CPU and a GPU). In addition, a plurality of functions may be realized by one processor. As a first example in which the plurality of functions are configured by one processor, there is an aspect in which one processor is configured by a combination of one or more CPUs and software, and the processor is realized as the plurality of functions, as represented by a computer such as an image processing device main body or a server. As a second example, there is an aspect in which a processor for realizing the functions of the entire system by one integrated circuit (IC) chip as represented by a system on chip (SoC) or the like is used. In this way, various functions are configured by using one or more of the above-described various processors as a hardware structure. Furthermore, the hardware structure of these various processors is, more specifically, an electric circuit (circuitry) in which circuit elements such as semiconductor elements are combined.

In a case where the above-described processor or electric circuit executes software (program), a processor (computer) readable code of the software to be executed is stored in a non-transitory recording medium such as a read only memory (ROM), and the processor refers to the software. The software stored in the non-transitory recording medium includes a program for inputting an image and measuring a subject. The code may be recorded on a non-transitory recording medium such as various types of magneto-optical recording device or a semiconductor memory instead of the ROM. In the processing using the software, for example, a random access memory (RAM) is used as a temporary storage area, and data stored in, for example, an electronically erasable and programmable read only memory (EEPROM) (not shown) can be referred to.

<Configuration of Operation Unit>

The processor 200 comprises the operation unit 208. The operation unit 208 comprises an operation mode setting switch (not shown) and the like, and can set the wavelength of the observation light (whether white light or narrow-band light is used, and which narrow-band light is used in a case of the narrow-band light). In addition, the operation unit 208 includes a keyboard and a mouse (not shown), and the user can perform setting operations of an imaging condition, a display condition, a moving image saving condition, and the like via these devices. These setting operations may be performed via a foot switch (not shown), or may be performed by sound, line-of-sight, gesture, or the like. The operation mode may be set by assigning an operation mode setting function to the function button 143 (refer to FIG. 1) of the hand operation part 102 as described above.

<Configuration of Storage Unit>

Figure 5:
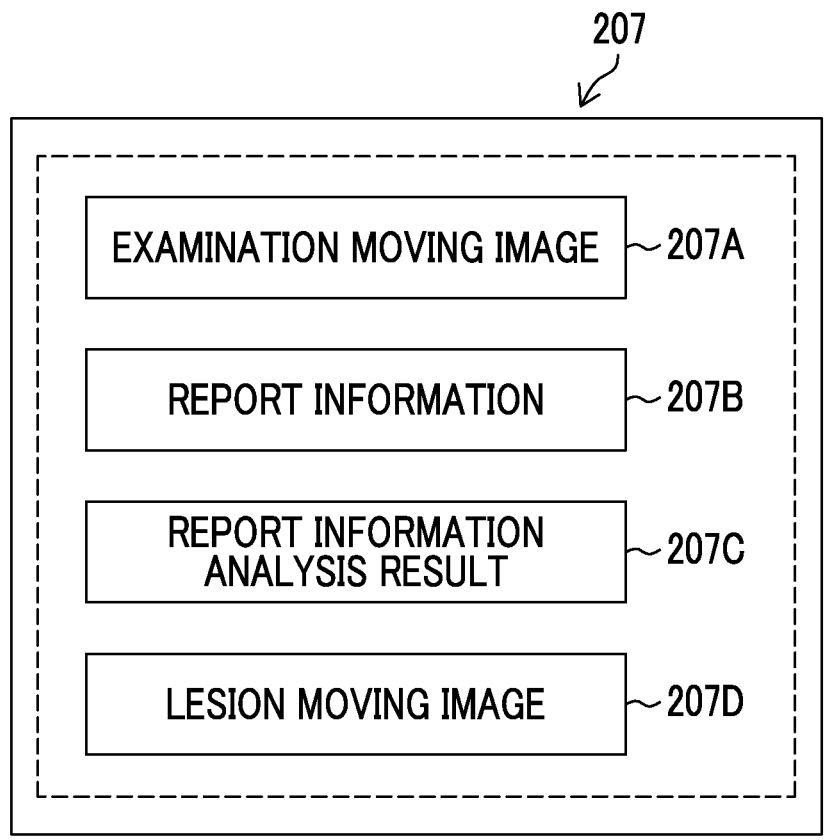
FIG. 5 is a diagram showing information saved in a storage unit.

The storage unit 207 (recording device) is configured to include various types of magneto-optical recording media and a non-transitory recording medium such as a semiconductor memory, and stores (saves) an examination moving image 207A, report information 207B, a report information analysis result 207C, and a lesion moving image 207D, as shown in FIG. 5. These images and information are displayed on the monitor 400 by an operation via the operation unit 208 and under control of the CPU 210 and/or the image processing unit 204.

In addition to the above-described images, an analysis result of any one or both of a region of attention (region of interest), which is a region to be noticed, included in an image for medical use (medical image) and presence or absence of a target to be noticed may be stored in the storage unit 207 (recording device). In this case, the image processing unit 204 (medical image analysis processing unit, medical image analysis result acquisition unit) can acquire the analysis results from the storage unit 207 and display the analysis results on the monitor 400.

<Configuration of Display Device>

The monitor 400 (display device) displays a moving image and/or a still image acquired by an examination, a lesion moving image, an imaging condition setting screen, a display condition setting screen, report information, information indicating an analysis result (extraction result) of the report information, and the like by the operation via the operation unit 208 and under the control of the CPU 210 and/or the image processing unit 204. In addition, the monitor 400 has a touch panel (not shown) for performing an imaging condition setting operation and/or a display condition setting operation.

<Image Processing Method>

Figure 6:
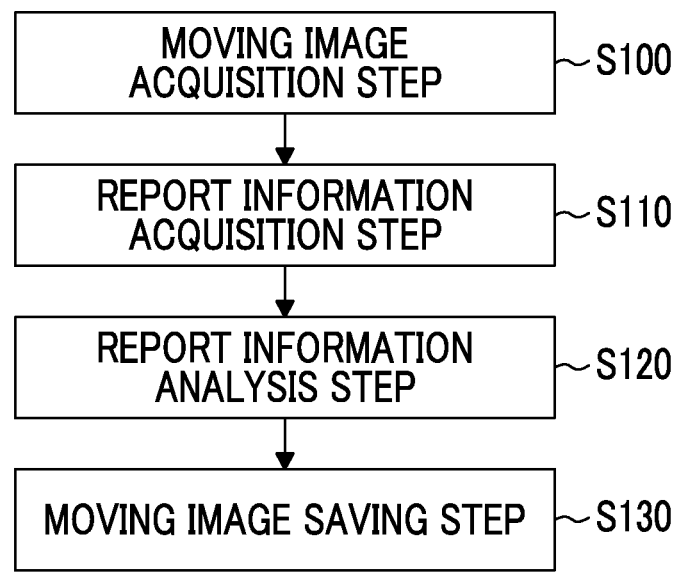
FIG. 6 is a flowchart showing processing of an image processing method.

The image processing method using the endoscope system 10 will be described. FIG. 6 is a flowchart showing processing of the image processing method according to the first embodiment.

<Acquisition of Examination Moving Image>

The moving image acquisition unit 204A acquires (captures) an examination moving image by the endoscope (step S100: moving image acquisition step). In the examination, the insertion part 104 is inserted into the subject, and the distal end rigid portion 116 is positioned at a desired portion by operating (pushing/pulling, bending vertically and horizontally, or the like) the hand operation part 102. The start and end of acquisition of a moving image may be automatically performed without a user operation, or may be performed according to a user operation on the imaging button 144 or the like. The acquisition of the examination moving image may be performed at the time of inserting the insertion part 104 or at the time of pulling out. The acquired examination moving image is saved in the storage unit 207 as the examination moving image 207A. In addition, the still image acquisition unit 204B captures a still image automatically or according to a user operation, and saves the still image in the storage unit 207.

<Acquisition of Report Information>

The report information acquisition unit 204C acquires report information on the examination corresponding to the examination moving image acquired in step S100 (step S110: report information acquisition step). The report information acquired in step S110 includes at least one of subject information of the still image acquired in the examination corresponding to the examination moving image or acquisition time information of the still image. In step S110, the user may acquire the report information 207B created by using the endoscope system 10 and stored in the storage unit 207 on the basis of the examination moving image, the still image, and the like acquired in step S100 (in this case, a report creation support function can be provided in the image processing unit 204), and a communication control unit 205 and the report information acquisition unit 204C may acquire information on a separately created report from an external server (not shown), database, or the like. In addition, the report information may include examination information. The examination information indicates patient information, doctor information, device information, lesion information (position, size, endoscopic findings, treatment status, pathological examination result, or the like), procedure information (insertion time and/or extraction time, sedative, treatment tool, coloring agent, or use status of image enhanced endoscopy (IEE)), or the like. The examination information may be information input by the user.

In step S110, information on the subject (position, size, type, and the like of the subject) shown in the image can be used as "subject information". Information that can specify the timing of a lesion image in a moving image, such as an absolute time when an image is captured (Japan Standard Time, or the like), an elapsed time from the start of capturing a moving image of a frame where an image is captured, or a count number of a counter corresponding to an imaging time can be used as "acquisition time information".

The "still image" included in the above-described report information includes many images in which a lesion (region of interest) is not shown. Therefore, in a case where the images before and after the acquisition of the still image are saved, the lesion may not be shown. Thus, in the first embodiment, as described below, information on a lesion image is extracted from the report information, and a lesion moving image, which is a moving image for a time range in which the lesion image is included, is saved on the basis of the analysis result (extraction result).

<Analysis of Report Information>

The report information analysis unit 204D extracts at least one of the subject information of the lesion image or the acquisition time information of the lesion image from the report information acquired in step S110 (step S120: report information analysis step). The information can be extracted by, for example, the report information acquisition unit 204C acquiring report information including lesion information indicating whether the still image is the lesion image, and the report information analysis unit 204D extracting subject information and/or acquisition time information of the lesion image on the basis of the acquired lesion information. The lesion information and the subject information and acquisition time information of the lesion image may be information input by the user into the report via the operation unit 208. The report information analysis unit 204D may extract subject information and/or acquisition time information of the lesion image from the examination information included in the report information.

<Saving of Lesion Moving Image>

Figure 7A:
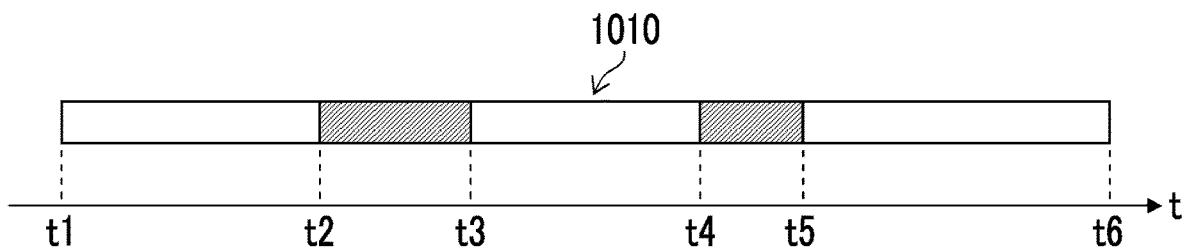
FIGS. 7A to 7C are diagrams showing examples of a saving pattern of a moving image.
Figure 7B:
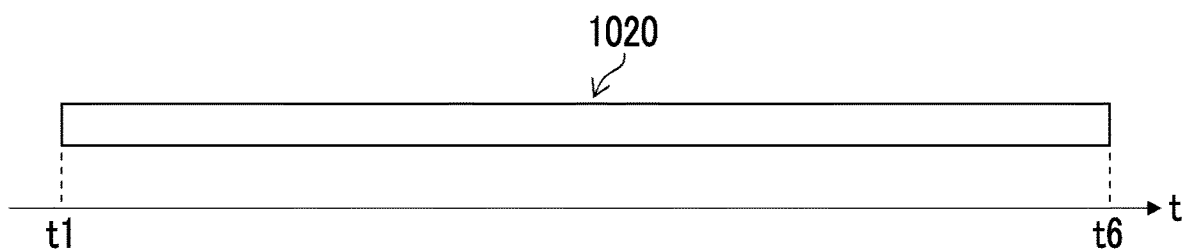
Figure 7C:
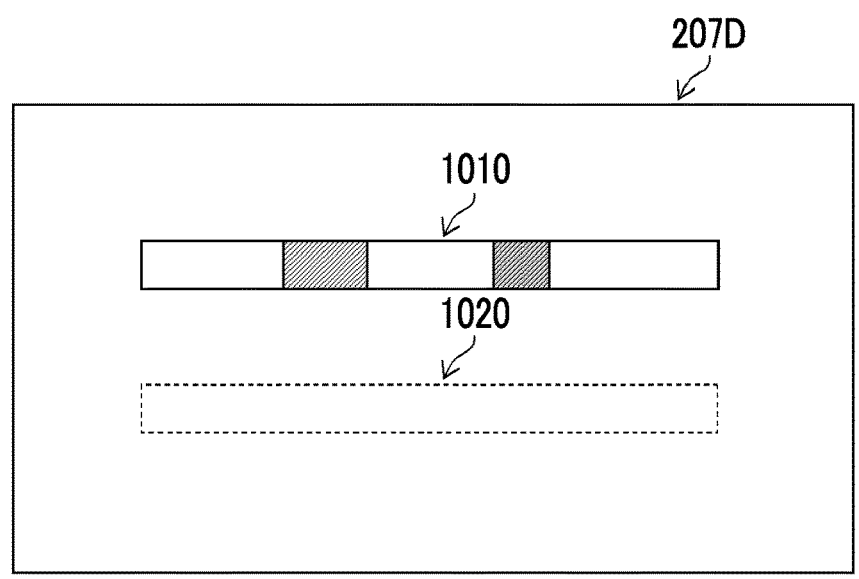

The moving image saving unit 204E saves a lesion moving image which is "a moving image for a time range in which the lesion image is included in the examination moving image" in the storage unit 207 as the lesion moving image 207D, on the basis of the analysis result (extraction result) of the above-described report information (step S130: moving image saving step). The moving image saving unit 204E can determine whether to save the lesion moving image on the basis of the result of the analysis (extraction) in step S120. Specifically, in a case where the report information includes the lesion image and/or the lesion information, the lesion moving image may be saved, and in a case where the report information does not include the lesion image and/or the lesion information, determination is made that "the examination moving image does not include a lesion (region of interest)" and the saving processing of the lesion moving image may be stopped. For example, as shown in FIG. 7A, in a case where the shaded portions (a portion from time t2 to time t3 and a portion from time t4 to time t5) of an examination moving image 1010 acquired ranging from time t1 to time t6 are in the time range in which a lesion is shown, the moving image saving unit 204E can save the examination moving image 1010 as a lesion moving image (moving image for a time range in which the lesion image is included), as shown in FIG. 7C. In contrast, as shown in FIG. 7B, in a case where no lesion is shown in an examination moving image 1020, the moving image saving unit 204E may not save the examination moving image 1020 (or deletes the image once saved), as shown in FIG. 7C.

<Detection of Specific Lesion and Saving of Lesion Moving Image According to Examination Content and the Like>

Regarding the lesion moving image, in addition to saving the examination in which the lesion is found as described above, the examination in which a specific lesion (lesion with low prevalence, difficult-to-detect case, or the like) is found may be saved on the basis of the acquisition result and the analysis result of the report information. For example, in a case where the size of the lesion is small, or in a case where the lesion has a flat shape and almost no ridge, the lesion moving image can be saved as a "lesion difficult to detect". For example, in a case where a pathological biopsy is performed (in this case, it is considered that "it is difficult to determine a lesion to be biopsied by endoscopic findings"), or in a case where there is inconsistency between results of the pathological biopsy and endoscopic findings (for example, endoscopic findings showed "suspected adenoma" and a biopsy was performed, but the pathological result was a hyperplastic polyp), the lesion moving image can be saved as a "lesion difficult to diagnose". Further, as will be described later, in a case where a learning device is constructed by machine learning using a lesion moving image as an input, the lesion moving image may be saved according to the purpose of use of the learning device. For example, it is conceivable that in a case where a learning device for a purpose of detecting (picking up) a lesion during screening is constructed, only the examination for screening purposes is saved (procedure videos such as endoscopic submucosal dissection (ESD) have a low utility value in machine learning), and in a case where a learning device for a purpose of discriminating stages of cancer (intramucosal cancer, advanced cancer, and the like) is constructed, only the lesion moving image for examination for therapeutic purposes such as ESD and endoscopic mucosal resection (EMR) is saved.

<Aspect of Saving Processing>

Figure 8A:
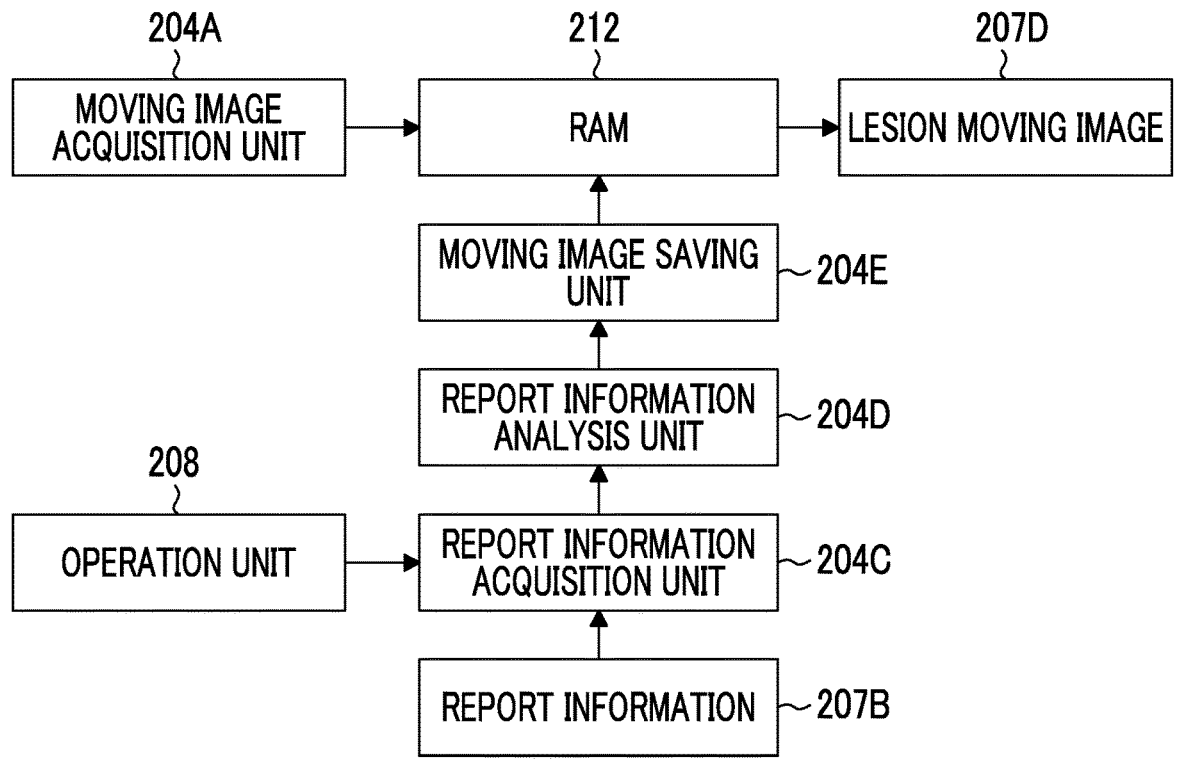
FIGS. 8A and 8B are diagrams showing processing for saving a moving image.
Figure 8B:
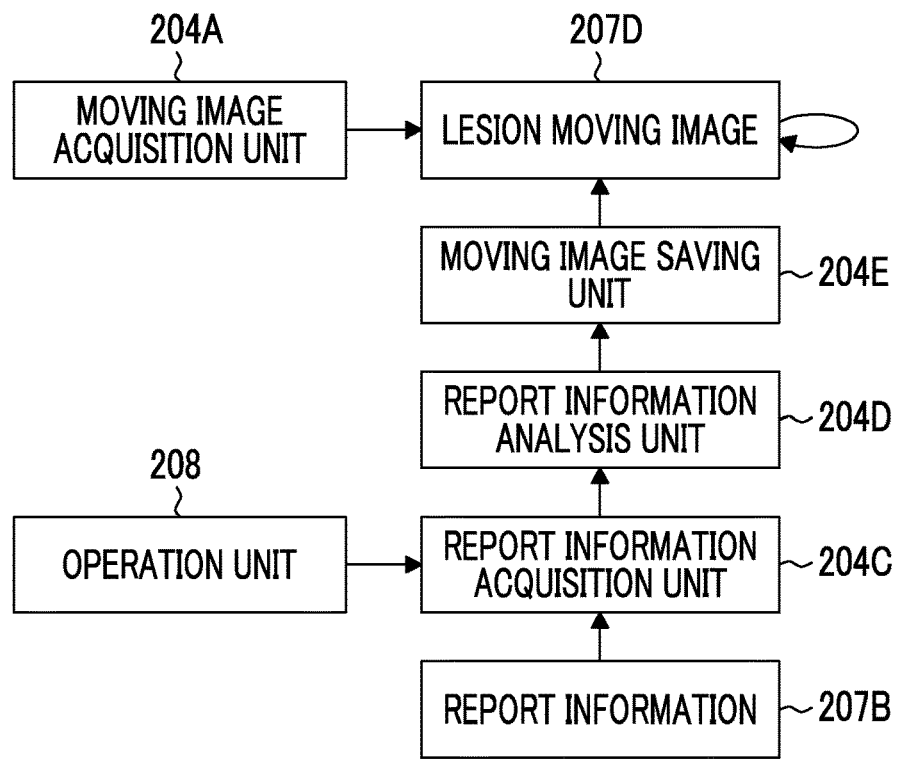

The processing in steps S100 to S130 can be performed, for example, in the following aspects. FIGS. 8A and 8B are diagrams showing a relationship between each unit of the endoscope system 10 and information used for processing in saving a lesion moving image. For example, as shown in FIG. 8A, the moving image acquisition unit 204A can temporarily save the examination moving image acquired in step S100 in the RAM 212, and the moving image saving unit 204E can save necessary portions in the storage unit 207 as the lesion moving image 207D (for the specific saving pattern, refer to FIGS. 9 to 12 described later). In addition, as shown in FIG. 8B, the moving image acquisition unit 204A (and the moving image saving unit 204E) may save the examination moving image acquired in step S100 in the storage unit 207 as the lesion moving image 207D, and the moving image saving unit 204E may delete unnecessary portions. As described above, the processing for saving the necessary portions (or deleting the unnecessary portions) can be performed by, for example, the report information analysis unit 204D (report information analysis unit) matching the subject information with the examination moving image to determine the time range in which the lesion image is included in the examination moving image and the moving image saving unit 204E saving the determined time range. Even in a case where there is no subject information, the lesion moving image can be saved when the acquisition time information of the lesion image can be extracted by analyzing the report information.

<Saving Pattern of Lesion Moving Image>

The saving pattern (it means the final saving form, regardless of which pattern in FIGS. 8A and 8B is used for processing) of the lesion moving image will be described below. Which of these patterns is used for processing may be determined by the image processing unit 204 without depending on the instruction of the user, or may be determined according to the instruction of the user via the operation unit 208.

(Pattern 1)

Figure 9A:
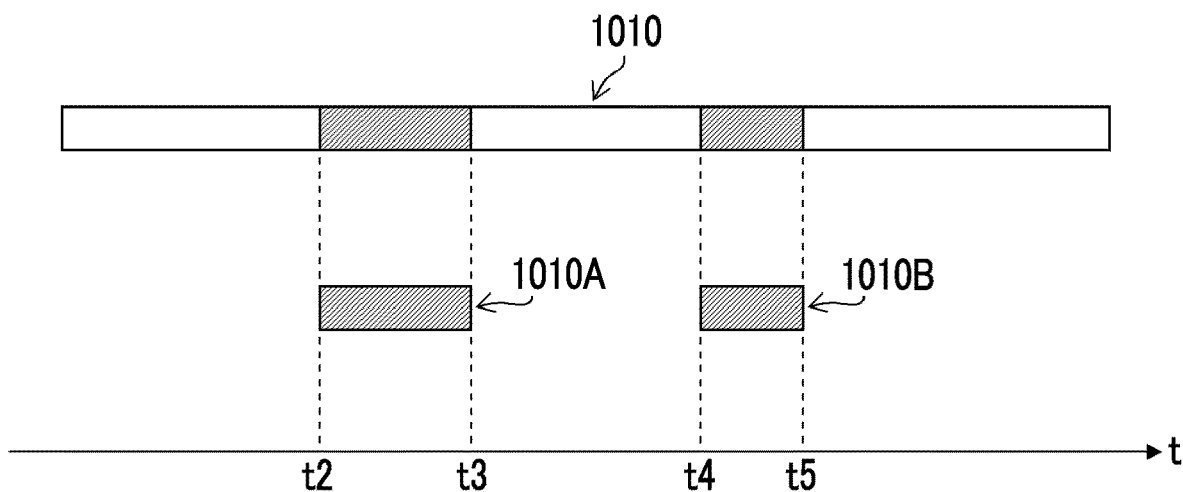
FIGS. 9A and 9B are diagrams showing other examples of the saving pattern of the moving image.
Figure 9B:
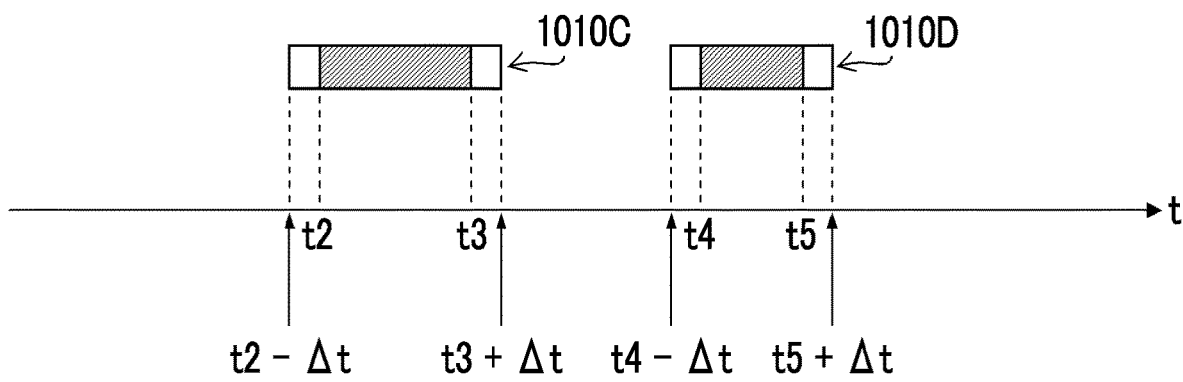

The moving image saving unit 204E can save temporally distant portions of the examination moving image as another moving image. For example, as shown in FIG. 9A, in the original examination moving image 1010, a portion from time t2 to time t3, in which the lesion is shown, can be saved in the storage unit 207 as one lesion moving image 1010A, and a portion from time t4 to time t5, in which the lesion is shown, can be saved as another lesion moving image 1010B. In this case, as shown in FIG. 9B, a lesion moving image 1010C ranging from (time t2−Δt) to (time t3+Δt) and/or a lesion moving image 1010D ranging from (time t4−Δt) to (time t5+Δt) may be saved (the period of Δt is a period in which no lesion is shown. The length of Δt can be set in consideration of restrictions on the amount of data of moving images). For the period of Δt, a part of the original examination moving image may be used, or an image created by image processing may be used.

Note that the moving image saving unit 204E may save each of time ranges in which different lesions are shown as an independent moving image in addition to or instead of saving the temporally distant portions as another moving image.

(Pattern 2)

Figure 10A:
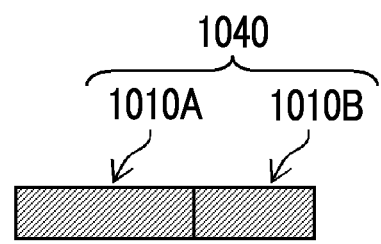
FIGS. 10A and 10B are diagrams showing still other examples of the saving pattern of the moving image.
Figure 10B:
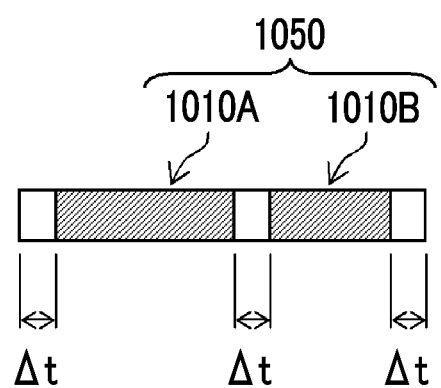

The moving image saving unit 204E can save the temporally distant portions of the examination moving image as one moving image. For example, the lesion moving images 1010A and 1010B shown in FIG. 9A can be collected and saved as one lesion moving image 1040 as shown in FIG. 10A. In this case, as in a lesion moving image 1050 shown in FIG. 10B, a period of length Δt (a period in which no lesion is shown) may be provided between the parts of the lesion moving images 1010A and 1010B.

<Association of Examination Moving Image and Lesion Moving Image>

Figure 11:
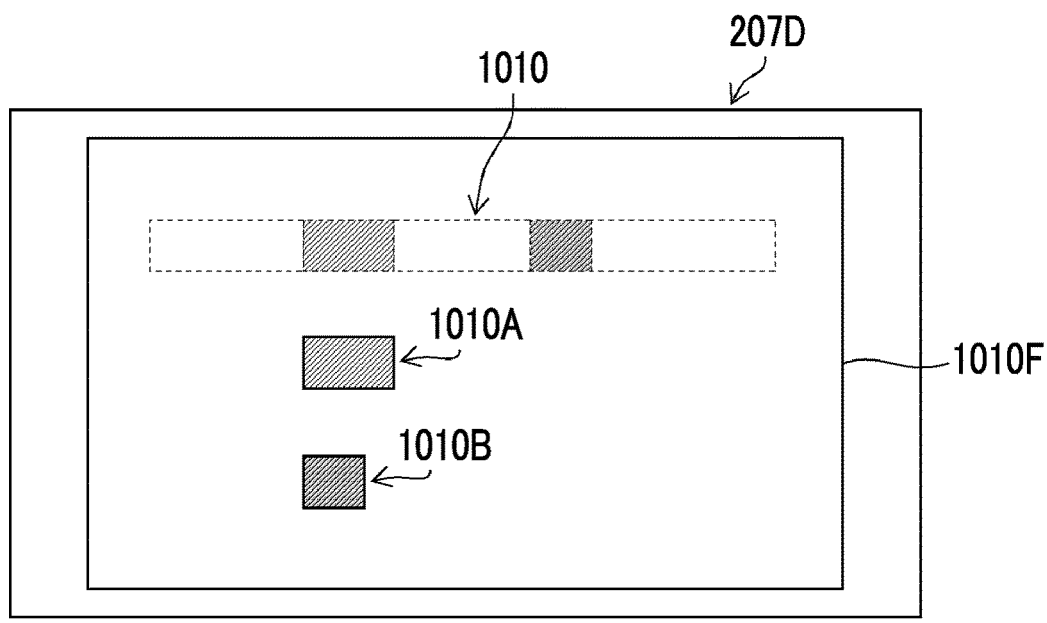
FIG. 11 is a diagram showing a state in which a lesion moving image is saved in the same folder as an original file.

In a case of saving the lesion moving image as described above, it is preferable to associate the original examination moving image and the lesion moving image in consideration of management and use of the image and the like. For example, in a case of saving a part of the examination moving image 1010 as independent lesion moving images 1010A and 1010B as shown in FIG. 9A, these images can be associated with each other by saving the lesion moving images 1010A and 1010B in the same folder 1010F (for example, a folder created for each examination or for each examination moving image, in which the examination moving image 1010 is saved) in the saving region (storage unit 207) of the lesion moving image 207D as shown in FIG. 11 (FIG. 11 shows a state in which the original examination moving image 1010 is deleted in accordance with the saving of the lesion moving images 1010A and 1010B). Even in a case where the examination moving image and the lesion moving image are saved in different folders, they can be associated by, for example, recording identification information of the original examination moving image and/or other lesion moving images in the header portion of the final lesion moving image file.

<Reduction of Data Capacity by Changing Frame Rate and the Like>

Figure 12:
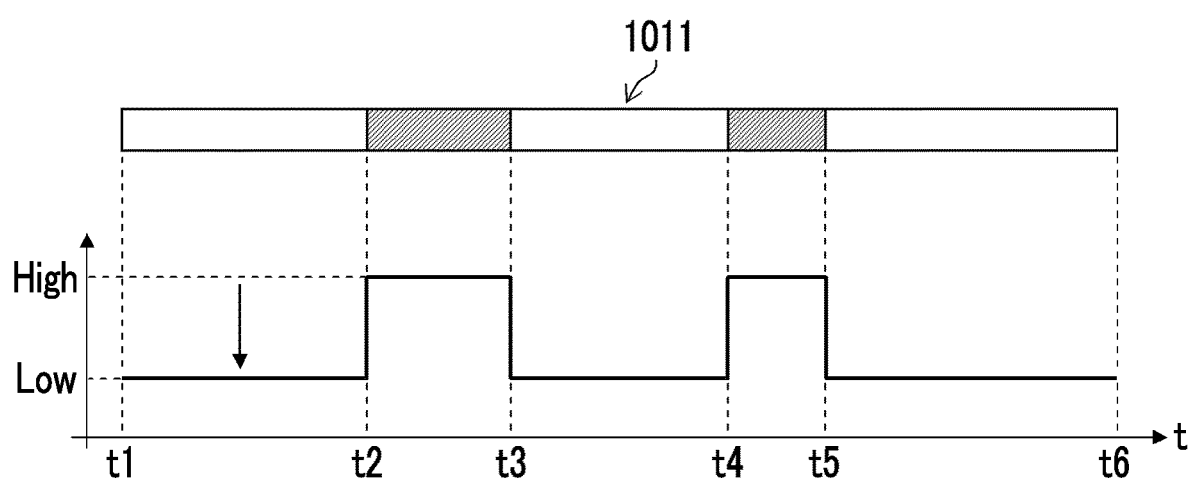
FIG. 12 is a diagram showing a state in which data capacity is reduced.

In a case of saving the lesion moving image for the examination moving image, the moving image saving unit 204E may save a small-capacity moving image having a smaller data capacity than the examination moving image by subjecting the examination moving image to processing for reducing a frame rate outside the time range in which the lesion image is included and/or processing for reducing a resolution outside the time range. For example, as shown in FIG. 12, the moving image saving unit 204E can save a small-capacity moving image 1011 (small-capacity moving image) having a smaller data capacity than the original examination moving image 1010 as a lesion moving image by subjecting the original examination moving image 1010 to processing for reducing the frame rate (or resolution) during a period in which no lesion is shown (outside the time range in which the lesion image is included: time t1 to time t2, time t3 to time t4, and time t5 to time t6 in FIG. 12) from High to Low. By such processing, the lesion moving image can be efficiently saved. The frame rate and/or the resolution may be changed not only in outside the time range in which the lesion image is included, but also in the time range in which the lesion image is included, according to the image content. For example, in a case where a specific lesion such as a lesion with low prevalence or a difficult-to-detect case is included, the frame rate and/or the resolution can be set relatively higher than in other cases. In this case, the same case as described above in the section "Detection of specific lesion and saving of lesion moving image according to examination content and the like" can be referred to as a "specific lesion". In addition, as described above in the same section, in a case where the lesion moving image is saved for a specific type of examination according to the purpose of machine learning, the frame rate and/or the resolution may be set relatively higher than that in the case where the lesion moving image is saved for other examinations.

As described above, in the endoscope system 10 according to the first embodiment, the lesion moving image can be efficiently saved.

<Construction of Learning Device Using Lesion Moving Image as Input>

Figure 13A:
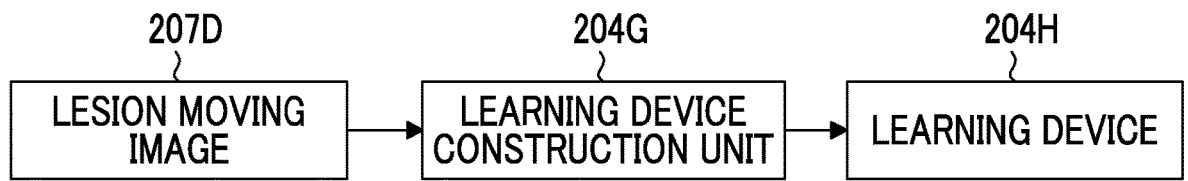
FIGS. 13A and 13B are diagrams showing a state in which a learning device is generated using a lesion moving image and a lesion is detected using the generated learning device.

It is possible to generate a learning device for automatic lesion detection by using the lesion moving image saved by the above processing as an input. For example, as shown in FIG. 13A, the lesion moving image 207D can be input as learning data, and a learning device construction unit 204G can construct a learning device 204H. In the case where the learning device 204H is constructed, the fact that it is a lesion, and/or the type of lesion may be attached to the image as a label and used as teacher data. The learning device construction unit 204G and the learning device 204H may be used as components of the endoscope system 10 (image processing unit 204) or independent devices may be used. As described above, since the endoscope system 10 saves the lesion moving image which is the moving image for the time range in which the lesion image is included in the examination moving image, it is possible to construct a learning device by efficiently learning with this lesion moving image as an input.

<Construction of Learning Device Using Deep Learning Algorithm>

The learning device construction unit 204G may construct a learning device using a deep learning method. For example, a learning device that analyzes whether a lesion is included in an input image may be constructed by performing image analysis processing using deep learning on a lesion moving image on the basis of a deep learning algorithm. The deep learning algorithm is a convolutional neural network method, that is, an algorithm for recognizing whether a lesion (region of interest) is included in the image through repetition of a convolutional layer and a pooling layer, a fully connected layer, and an output layer.

<Detection of Lesion>

Figure 13B:
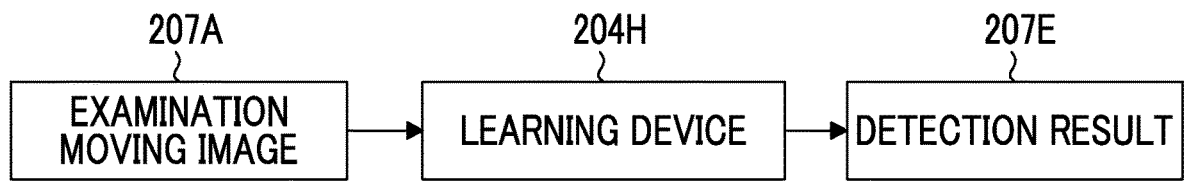

Using the learning device 204H constructed as described above, the lesion can be detected from the examination moving image. FIG. 13B shows a state in which the examination moving image 207A acquired in the examination is input to the learning device 204H and a detection result 207E regarding a lesion (region of interest) is obtained. Examples of lesions detected by the learning device 204H include polyps, cancers, diverticula of the large intestine, inflammations, treatment scars (endoscopic mucosal resection (EMR) scar, endoscopic submucosal dissection (ESD) scar, clip portions, and the like), bleeding points, perforations, vascular atypia, and the like.

<Classification of Lesion>

The learning device 204H may be used to classify the lesion detected from the examination moving image 207A. Examples of classification include classification of polyp (neoplastic or non-neoplastic), diagnosis of the stage of cancer, current location in the lumen (pharynx, esophagus, stomach, duodenum, or the like in the upper part, and cecum, ascending colon, transverse colon, descending colon, sigmoid colon, rectum, or the like in the lower part), and the like. The classification of the lesion may be performed integrally with the detection.

<Display Example of Image>

In the endoscope system 10, the display control unit 204F can cause the monitor 400 (display device) to display images such as the examination moving image 207A, the lesion moving image 207D, and a still image captured automatically or according to a user operation. Processing for detecting a lesion from the image may be performed in the case where the image is displayed, and the lesion may be identified and displayed according to the detection result. This detection processing can be performed by providing the image processing unit 204 with a detection unit using a known computer aided diagnosis (CAD) system, the above-described learning device, and the like.

Figure 14:
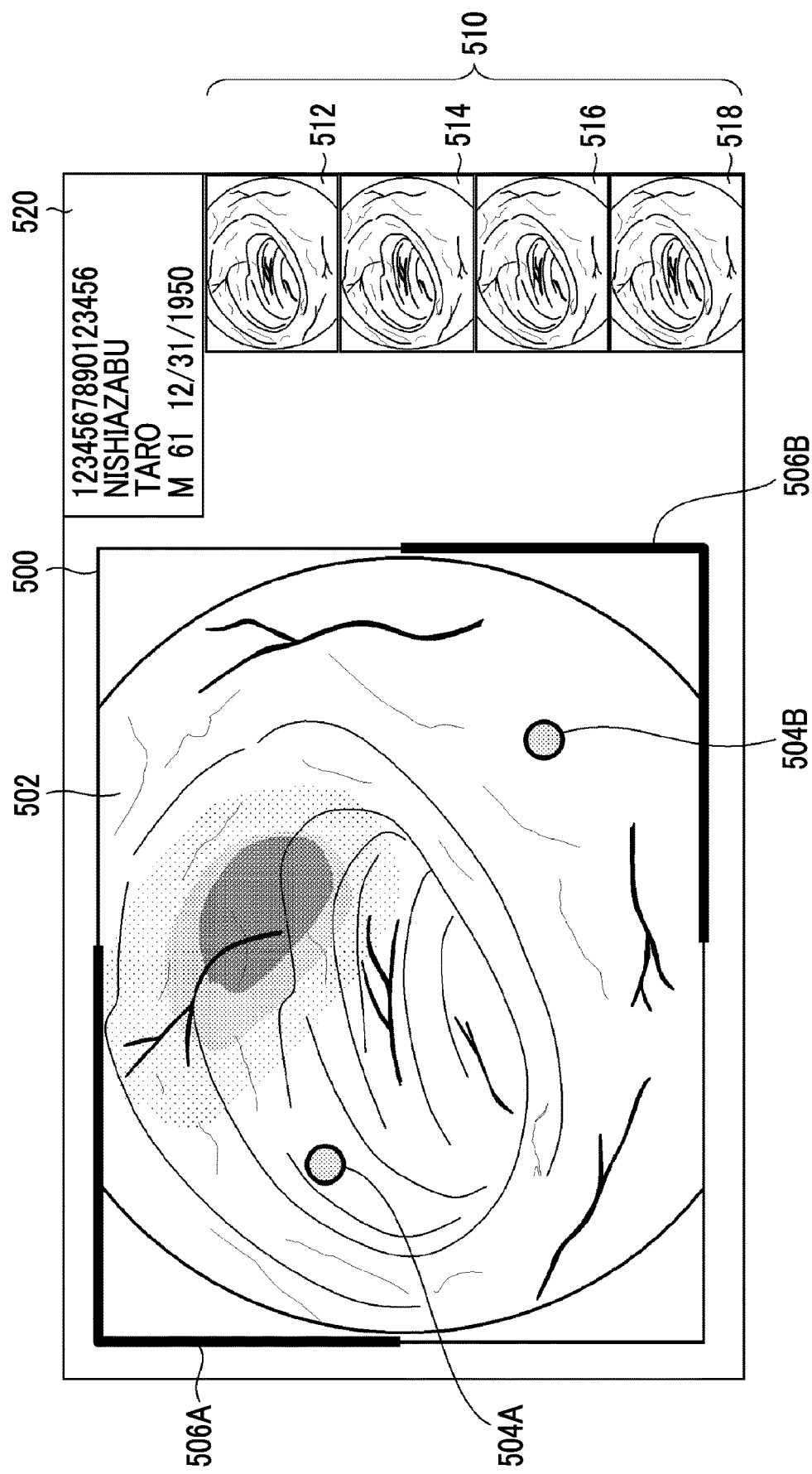
FIG. 14 is a diagram showing an example of identifying and displaying a lesion.

As shown in the example of FIG. 14, the display control unit 204F can cause the monitor 400 to display a first image display area 500, a second image display area 510, and a patient information display area 520. In the example of FIG. 14, an image 502 is displayed in the first image display area 500, and polyps 504A and 504B are detected in the image 502. In the second image display area 510, images 512 to 518 captured at a different time from the image 502 are displayed. In the example of FIG. 14, frames 506A and 506B are displayed for the polyps 504A and 504B, respectively. As shown in FIG. 14, the display control unit 204F displays the frame 506A on the edge of the second quadrant of the first image display area 500 and displays the frame 506B on the edge of the fourth quadrant (first to fourth quadrants are based on the center of the first image display area 500). By displaying the frames 506A and 506B as shown in FIG. 14, the user can easily recognize the polyps 504A and 504B. In addition, since the frames 506A and 506B are displayed at the edge of the first image display area 500, the frames 506A and 506B do not block the image 502, and the user can smoothly perform observation and diagnosis.

Figure 15:
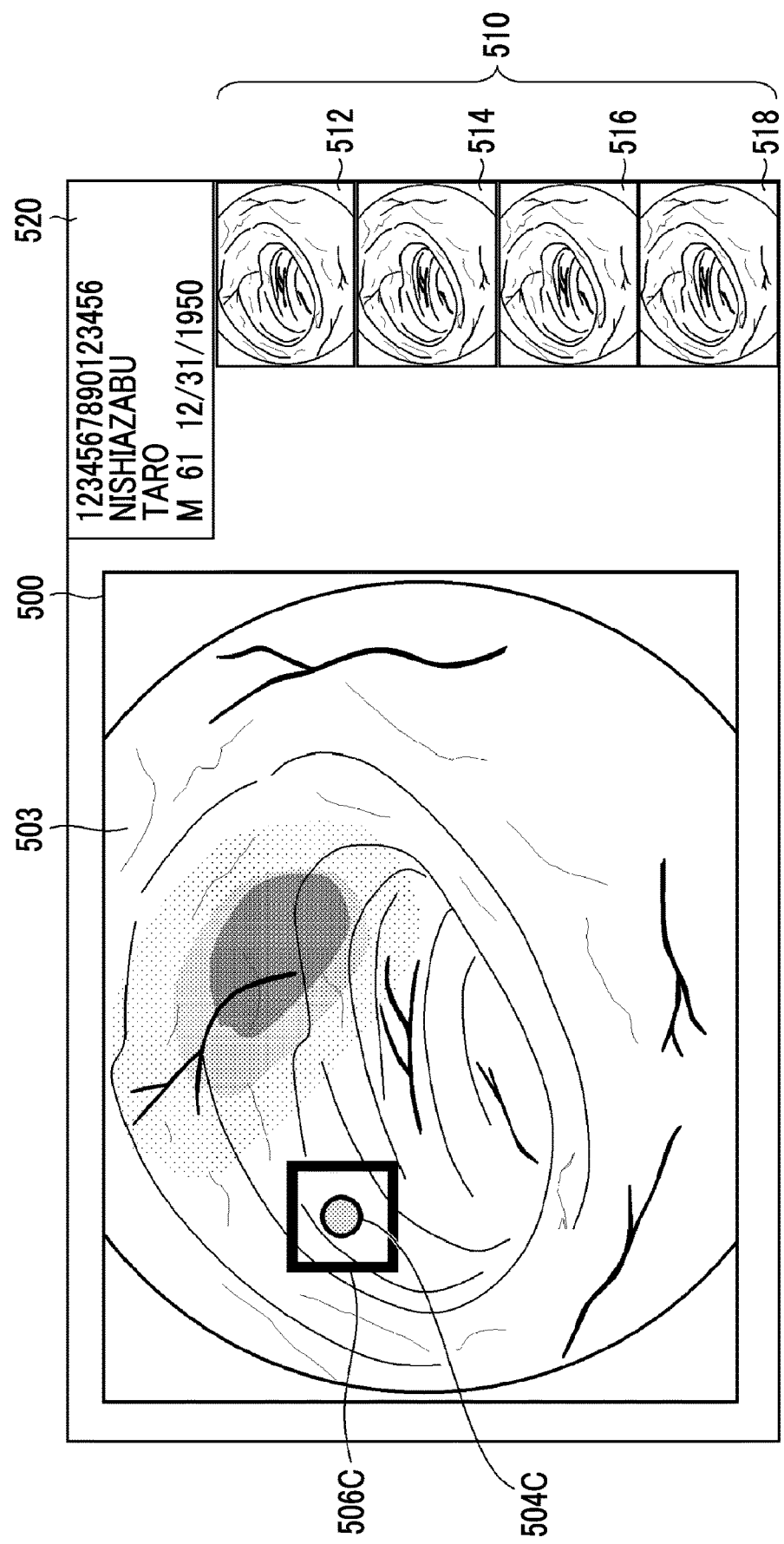
FIG. 15 is a diagram showing another example of identifying and displaying the lesion.

FIGS. 15 and 16 are diagrams showing other examples of image display. As shown in FIG. 15, by enclosing a polyp 504C in an image 503 with a frame 506D, the position of the polyp 504C can be clearly presented. In this case, when the polyp 504C is detected, the frame 506C is highlighted (for example, by a thick line) and displayed as shown in FIG. 15, and when a certain time has elapsed since the detection (for example, about several seconds), the degree of highlight is lowered and displayed as shown in FIG. 16 (for example, a thin line like the frame 506D is displayed, or the display is gradually darkened or gradually erased). Therefore, the display of the frame can be prevented from obstructing the observation and diagnosis.

The frame described above can be displayed according to the number, position, size, and the like of the detected polyps (lesions). For example, in a case where a polyp (lesion) is detected in the first and third quadrants of the image 502 in the aspect of FIG. 14, a frame can be displayed at the edges of the first and third quadrants of the first image display area 500. In addition, in a case where a plurality of polyps are detected in the aspects of FIGS. 15 and 16, the same frame as in the examples of FIGS. 15 and 16 can be displayed for each polyp. The display conditions such as the color, brightness, and thickness of these frames may be set according to a user operation, or may be set by the display control unit 204F regardless of a user operation. Note that, in a case where a moving image is displayed on the monitor 400, lesions are continuously detected (for example, for each frame of the moving image), and the number, position, size, and the like of the frames can be changed and displayed according to the detection result.

(Additional Remark)

In addition to each aspect of the above-described embodiment, configurations to be described below are also included in the scope of the present invention.

(Additional Remark 1)

A medical image processing device comprising: a medical image analysis processing unit that detects a region of attention, which is a region to be noticed, on the basis of a feature quantity of pixels of a medical image; and a medical image analysis result acquisition unit that acquires an analysis result of the medical image analysis processing unit.

(Additional Remark 2)

The medical image processing device, in which the medical image analysis processing unit detects presence or absence of a target to be noticed, on the basis of the feature quantity of pixels of the medical image, and the medical image analysis result acquisition unit acquires an analysis result of the medical image analysis processing unit.

(Additional Remark 3)

The medical image processing device, in which the medical image analysis result acquisition unit acquires an analysis result of the medical image from a recording, and the analysis result includes any one or both of the region of attention, which is a region to be noticed, included in the medical image and the presence or absence of the target to be noticed.

(Additional Remark 4)

The medical image processing device, in which the medical image is a normal light image obtained by irradiation with light in a white range or light in a plurality of wavelength ranges as the light in the white range.

(Additional Remark 5)

The medical image processing device, in which the medical image is an image obtained by irradiation with light in a specific wavelength range, and the specific wavelength range is a range narrower than a white wavelength range.

(Additional Remark 6)

The medical image processing device, in which the specific wavelength range is a blue range or a green range of a visible range.

(Additional Remark 7)

The medical image processing device, in which the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

(Additional Remark 8)

The medical image processing device, in which the specific wavelength range is a red range of a visible range.

(Additional Remark 9)

The medical image processing device, in which the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

(Additional Remark 10)

The medical image processing device, in which the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

(Additional Remark 11)

The medical image processing device, in which the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

(Additional Remark 12)

The medical image processing device, in which the medical image is an in-vivo image that the inside of a living body is captured, and the in-vivo image has information on fluorescence emitted by a fluorescent material in the living body.

(Additional Remark 13)

The medical image processing device, in which the fluorescence is obtained by irradiating the inside of the living body with excitation light which has a peak in a range of 390 nm to 470 nm.

(Additional Remark 14)

The medical image processing device, in which the medical image is an in-vivo image that the inside of a living body is captured, and the specific wavelength range is an infrared wavelength range.

(Additional Remark 15)

The medical image processing device, in which the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

(Additional Remark 16)

The medical image processing device, in which the medical image acquisition unit comprises the special light image acquisition unit that acquires a special light image having information on a specific wavelength range on the basis of a normal light image obtained by irradiation with light in a white range or light in a plurality of wavelength ranges as the light in a white range, and the medical image is a special light image.

(Additional Remark 17)

The medical image processing device, in which a signal of the specific wavelength range is obtained by calculation based on color information of RGB or CMY included in the normal light image.

(Additional Remark 18)

The medical image processing device further comprising: a feature quantity image generation unit that generates a feature quantity image by calculation based on at least one of a normal light image obtained by irradiation with light in a white range or light in a plurality of wavelength ranges as the light in the white range or a special light image obtained by irradiation with light in a specific wavelength range, in which the medical image is a feature quantity image.

(Additional Remark 19)

An endoscope device comprising: the medical image processing device according to any one of Additional remarks 1 to 18; and an endoscope that acquires an image obtained by irradiation with at least one of light in a white wavelength range or light in a specific wavelength range.

(Additional Remark 20)

A diagnosis support device comprising: the medical image processing device according to any one of Additional remarks 1 to 18.

(Additional Remark 21)

A medical service support device comprising: the medical image processing device according to any one of Additional remarks 1 to 18.

Although the embodiments and other aspects of the present invention have been described above, the present invention is not limited to the above-described aspects, and various modifications can be made without departing from the spirit of the present invention.

EXPLANATION OF REFERENCES

10: endoscope system
100: endoscope main body
102: hand operation part
104: insertion part
106: universal cable
108: light guide connector
112: flexible portion
114: bendable portion
116: distal end rigid portion
116A: distal end side end surface
123: illumination part
123A: illuminating lens
123B: illuminating lens
126: forceps port
130: imaging optical system
132: imaging lens
134: imaging element
136: drive circuit
138: AFE
141: air supply and water supply button
142: suction button
143: function button
144: imaging button
170: light guide
200: processor
202: image input controller
204: image processing unit
204A: moving image acquisition unit
204B: still image acquisition unit
204C: report information acquisition unit
204D: report information analysis unit
204E: moving image saving unit
204F: display control unit
204G: learning device construction unit
204H: learning device
205: communication control unit
206: video output unit
207: storage unit
207A: examination moving image
207B: report information
207C: report information analysis result
207D: lesion moving image
207E: detection result
208: operation unit
209: sound processing unit
209A: speaker
210: CPU
211: ROM
212: RAM
300: light source device
310: light source
310B: blue light source
310G: green light source
310R: red light source
330: stop
340: condensing lens
350: light source control unit
400: monitor
500: first image display area
502: image
503: image
504A: polyp
504B: polyp
504C: polyp
506A: frame
506B: frame
506C: frame
506D: frame
510: second image display area
512: image
514: image
516: image
518: image
520: patient information display area
1010: examination moving image
1010A: lesion moving image
1010B: lesion moving image
1010C: lesion moving image
1010D: lesion moving image
1010F: folder
1011: small-capacity moving image
1020: examination moving image
1040: lesion moving image
1050: lesion moving image
S100 to S130: each step of image processing method

What is claimed is:

1. An image processing device comprising one or more processors configured to:
   acquire an examination moving image by an endoscope in an examination;
   acquire report information on the examination corresponding to the examination moving image, the report information including at least one of subject information of a still image acquired in the examination or acquisition time information of the still image;
   extract at least one of subject information of a lesion image or acquisition time information of the lesion image from the report information; and
   save a lesion moving image, which is a moving image for a time range in which the lesion image is included in the examination moving image, on the basis of a result of the extraction,
   wherein the one or more processors determine whether to save the lesion moving image on the basis of the at least one of the extracted subject information of the lesion image or the extracted acquisition time information of the lesion image.

2. The image processing device according to claim 1,
   wherein the one or more processors are further configured to acquire the report information including lesion information indicating whether the still image is the lesion image, and
   extract the subject information and/or the acquisition time information of the lesion image on the basis of the lesion information.

3. The image processing device according to claim 1,
   wherein the one or more processors are further configured to match the subject information included in the report information with the examination moving image to determine the time range in which the lesion image is included in the examination moving image, and
   save the lesion moving image for the determined time range.

4. The image processing device according to claim 1,
   wherein the one or more processors are further configured to extract the acquisition time information of the lesion image, and
   save the examination moving image on the basis of the extracted acquisition time information.

5. The image processing device according to claim 1,
   wherein the one or more processors are further configured to acquire acquisition time information input by a user as the acquisition time information of the still image, and
   extract the acquisition time information as the acquisition time information of the lesion image.

6. The image processing device according to claim 1,
   wherein the one or more processors are further configured to save each of time ranges in which different lesions are shown in the examination moving image as an independent moving image.

7. The image processing device according to claim 1,
   wherein in a case of saving the lesion moving image for the examination moving image, the one or more processors are further configured to save a small-capacity moving image having a smaller data capacity than the examination moving image by subjecting the examination moving image to processing for reducing a frame rate outside the time range and/or processing for reducing a resolution outside the time range.

8. An endoscope system comprising:
   the image processing device according to claim 1;
   an endoscope including an insertion part to be inserted into a subject and a hand operation part connected to a proximal end of the insertion part, the insertion part including a distal end rigid portion, a bendable portion connected to a proximal end of the distal end rigid portion, and a flexible portion connected to a proximal end of the bendable portion; and
   an imaging optical system including an imaging lens that is provided in the distal end rigid portion to form an optical image of the subject, and an imaging element on which the optical image is formed by the imaging lens,
   wherein the one or more processors acquire the examination moving image captured by the imaging optical system.

9. An image processing method comprising:
   acquiring an examination moving image by an endoscope in an examination;
   acquiring report information on the examination corresponding to the examination moving image, the report information including at least one of subject information of a still image acquired in the examination or acquisition time information of the still image;
   extracting at least one of subject information of a lesion image or acquisition time information of the lesion image from the report information; and
   saving a lesion moving image, which is a moving image for a time range in which the lesion image is included in the examination moving image, on the basis of a result of the extraction,
   wherein, whether to save the lesion moving image is determined on the basis of the at least one of the extracted subject information of the lesion image or the extracted acquisition time information of the lesion image.

* * * * *